(12) United States Patent
Tanaka

(10) Patent No.: US 6,564,256 B1
(45) Date of Patent: *May 13, 2003

(54) IMAGE TRANSFER SYSTEM

(75) Inventor: Nobuyuki Tanaka, Kanagawa-ken (JP)

(73) Assignee: Fuji Photo Film Co., Ltd., Kanagawa-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/281,963

(22) Filed: Mar. 31, 1999

(30) Foreign Application Priority Data

Mar. 31, 1998 (JP) ............................................. 10-087138
Mar. 31, 1998 (JP) ............................................. 10-087140

(51) Int. Cl.[7] ............................................. G06F 13/00
(52) U.S. Cl. ........................ 709/219; 709/203; 709/328
(58) Field of Search ................................ 709/203, 213, 709/214, 217, 219, 223, 224, 225, 226, 328; 707/10

(56) References Cited

U.S. PATENT DOCUMENTS 5,986,662 A * 11/1999 Argiro et al. ............... 345/424
6,101,407 A * 8/2000 Groezinger ................. 600/407
6,115,486 A * 9/2000 Cantoni ...................... 382/128
6,226,412 B1 * 5/2001 Schwab ...................... 382/232
6,253,214 B1 * 6/2001 Hall et al. .................. 707/204
6,272,470 B1 * 8/2001 Teshima ........................ 705/3
6,349,330 B1 * 2/2002 Bernadett et al. ........... 709/219

* cited by examiner

*Primary Examiner*—Viet D. Vu
(74) *Attorney, Agent, or Firm*—Sughrue Mion, PLLC

(57) ABSTRACT

In order to effect data transfer at a high efficiency in an image transfer system where medical image data is transferred between a terminal and an image server on a DICOM standard communication system, a relay server is provided between a terminal and an archiver or a data base. When a request for transfer of medical image data is input into the terminal and sent to the relay server, the relay server sends a request for transfer of the medical image data to the archiver as requested from the terminal. The archiver transfers the desired medical image data to the relay server. The relay server stores the medical image data in a cache and transfers the same to the terminal. Thus the terminal can display the medical image data on a CRT or the like.

14 Claims, 2 Drawing Sheets

PRIOR ART

IMAGE TRANSFER SYSTEM

BACKGROUND OF THE INVENTION

1. Field of the Invention

This invention relates to an image transfer system, and more particularly to an image transfer system which transfers medical image data on a DICOM (Digital Imaging and Communication in Medicine) standard communication system.

2. Description of the Related Art

In the field of medical images, there has been a demand for a system which makes it feasible to transfer medical images between a plurality of systems and use the transferred images for diagnosis, for instance, a system which makes it feasible to store a CT image of company A and a MRI image of company B in an image server of company C and to reproduce for diagnosis the CT image or the MRI image on a CRT by a work station of company D connected to the image server through a network, or a system which makes it feasible to transfer a radiation image of company E to a work station of hospital F and display the result of diagnosis at the hospital F by a CRT of company G and output as a hard copy on film by a printer of company H. However, since the standard for handling medical image data from company to company, when transferring medical image data from a system of one company to a system of another company, the medical image data must be converted so as to conform to the system of the latter company, which deteriorates diagnostic efficiency.

Recently, the aforesaid DICOM standard has come to be used as a common standard for transferring medical image data. Since the DICOM standard supports TCP/IP protocol which is a current communication standard for Internet, by use of the DICOM standard, information on patients and/or medical image data can be transferred by way of a network between systems manufactured by different makers, whereby various drawbacks inherent to the conventional medical image handling system where medical images are recorded on photosensitive material and transferred in this state, e.g., that a large space is required to store medical images, fear of a loss of the film, that it takes a long time to transfer the film, and the like, can be overcome.

FIG. 5 shows a conventional medical image transfer system which transfers medical images on the DICOM standard. The medical image transfer system shown in FIG. 5 comprises an image server in which a plurality of medical images are stored and a plurality of terminals connected to the image server by way of a network. A request for a medical image (will be referred to as "image request", hereinbelow) is sent to the image server from each terminal and the image server transfers to each terminal medical image data requested by the terminal. Conversely, it is possible to transfer medical image data created at each terminal to the image server and store the medical image data in the image server.

However in the communication between the terminals and the image server on the DICOM standard, since each terminal can send the image request to only one image server, when the requested image is not stored in the image server, the terminal must send the image request to another image server after it receives a message describing the condition and accordingly the efficiency in transfer of medical image data is low. Further even if the requested image is stored in the image server, the image transfer speed becomes low when access to the same image server is made by a plurality of terminals at one time.

As the protocol for transfer of a multimedia on Internet, there have been in wide use http protocol and ftp protocol and web browser which is software for displaying a multimedia by use of such a protocol has been wide used owing to its inexpensiveness. However software and hardware for displaying and transferring medical image data on the aforesaid DICOM standard communication system must support protocol for the DICOM standard and accordingly are very particular and very expensive. Further in order to carry out transfer of medical image data on the DICOM standard, an exclusive network is required and the construction cost of the network is high.

SUMMARY OF THE INVENTION

In view of the foregoing observations and description, the primary object of the present invention is to provide an image transfer system which can efficiently transfer medical image data.

Another object of the present invention is to provide an image transfer system which can efficiently transfer medical image data at low cost on a DICOM standard communication system.

In accordance with a first aspect of the present invention, there is provided an image transfer system comprising
  one or more image servers which store medical image data, and
  at least one terminal for instructing transfer of the medical image data from the image server to the terminal and/or transfer of the medical image data from the terminal to the image server on a DICOM standard communication system,
  wherein the improvement comprises
  a relay server which intervenes between the terminal and the image servers and makes access to one of the image servers on the basis of instruction from the terminal to execute transfer of the medical image data.

In this specification, the term "medical image data" should be broadly interpreted to sometimes include information on diagnosis of the patient and the like.

It is preferred that the image transfer system of the first aspect of the present invention be provided with a plurality of said relay servers.

Further it is preferred that the relay server be provided with a cache for accumulating therein a plurality of pieces of medical image data.

In accordance with a second aspect of the present invention, there is provided an image transfer system comprising
  one or more image servers which store medical image data, and
  at least one terminal for instructing transfer of the medical image data from the image server to the terminal and/or transfer of the medical image data from the terminal to the image server on a DICOM standard communication system,
  wherein the improvement comprises
  a relay server which intervenes between the terminal and the image servers, receives transfer of medical image data prior to instruction from the terminal, and is provided with a cache for accumulating therein a plurality of pieces of medical image data.

In this specification, the expression "the relay server receives transfer of medical image data" should be interpreted to include that an image server and/or a system for creating medical image data makes access to the relay server and transfers medical image data to the relay server as well as that the relay server spontaneously makes access to the image servers and receives transfer of medical image data. For example, the relay server may periodically access to the image servers and receive transfer of medical image data newly stored in the image servers, or the relay server may receive transfer of newly created medical image data when the newly created medical image data is transferred from the system for creating medical image data to the image servers by way of the relay server.

It is preferred also in the image transfer system of the first aspect of the present invention that the image transfer system be provided with a plurality of said relay servers.

In accordance with a third aspect of the present invention, there is provided an image transfer system comprising one or more image servers which store medical image data, and at least one terminal for instructing transfer of the medical image data from the image server to the terminal and/or transfer of the medical image data from the terminal to the image server on a DICOM standard communication system, wherein the improvement comprises a protocol conversion server which intervenes between the terminal and the image servers, transfers medical image data, transferred from the image servers, to the terminal after converting the DICOM standard protocol of the medical image data to a generalized protocol, and transfers medical image data, transferred from the terminal, to the image servers after converting a generalized protocol of the medical image data to the DICOM standard protocol.

The "generalized protocol" is http protocol, ftp protocol or the like used on Internet.

It is preferred that the image transfer system of the third aspect of the present invention be provided with a plurality of said protocol conversion servers.

Further it is preferred that the protocol conversion server be provided with a cache.

Further it is preferred that the protocol conversion server converts the format of the medical image data to a predetermined format and transfers the converted medical image data to the terminal.

The expression "converts the format of the medical image data to a predetermined format" means, for instance, to, when the medical image data is in a format which cannot be displayed by the terminal, convert the format of the medical image data to a format which can be displayed by the terminal, to, when the medical image data is too large in data size, compress the data size of the medical image data, and to convert the medical image data to a HTML document so that the medical image and the diagnosis information and the like can be displayed simultaneously by the terminal.

The image transfer system of the first aspect of the present invention is characterized in that a relay server which makes access to one of the image servers on the basis of instruction from the terminal to execute transfer of the medical image data on a DICOM standard communication system is connected between the terminal and the image servers. The relay server sends request for transfer of desired medical image data to one of the image servers according to instruction from the terminal and when the desired medical image data is not in the image server the relay server sends the request to another image server. Then the relay server receives the desired medical image data from one of the image servers and transfers the desired medical image data to the terminal. Accordingly, the terminal need not send the request designating an image server but can receive a desired medical image data by simply sending the request to a designated relay server, whereby the terminal can efficiently executes transfer of medical image data.

Further by providing the image transfer system with a plurality of such relay servers, when a plurality of requests are sent to a relay server from a plurality of terminals at one time, the relay server can distribute the requests to other relay servers, whereby transfer of medical image data can be executed at a high efficiency. Further even if one of the relay servers fails, the other relay servers can act for the fault relay server.

By providing the relay server with a cache for accumulating therein a plurality of pieces of medical image data, the relay server can store medical image data, once transferred to a terminal, in the cache and can transfer the medical image data to another terminal immediately after receipt of request from the terminal, whereby transfer of medical image data can be executed at a higher efficiency.

The image transfer system of the second aspect of the present invention is characterized in that the image transfer system is provided with a relay server which intervenes between the terminal and the image servers, receives transfer of medical image data prior to instruction from the terminal, and is provided with a cache for accumulating therein a plurality of pieces of medical image data. With this arrangement, the relay server can transfer a desired medical image data immediately after receipt of request from the terminal, whereby transfer of medical image data can be executed at a higher efficiency.

The image transfer system of the third aspect of the present invention is characterized in that the image transfer system is provided between the terminal and the image servers with a protocol conversion server which converts the DICOM standard protocol to a generalized protocol such as http, ftp and the like. With this arrangement, the medical image data on the DICOM standard protocol transferred to the protocol conversion server from the image server is converted to medical image data on a generalized protocol by the protocol conversion server and is transferred to the terminal. Accordingly, the terminal can display the medical image data by inexpensive web browser which supports the generalized protocol. The medical image data on the generalized protocol transferred to the protocol conversion server from the terminal is converted to medical image data on the DICOM standard protocol by the protocol conversion server and is transferred to the image server. Accordingly, medical image data can be observed through an inexpensive system such as a general-purpose personal computer at the terminal and medical image data can be transferred through Internet, whereby an exclusive network is unnecessary and the system can be formed at low cost.

Further by providing the image transfer system with a plurality of such protocol conversion servers, when a plurality of requests are sent to a protocol conversion server from a plurality of terminals at one time, the protocol conversion server can distribute the requests to other protocol conversion servers, whereby transfer of medical image data can be executed at a high efficiency. Further even if one of the protocol conversion servers fails, the other protocol conversion servers can act for the fault protocol conversion server.

By providing the protocol conversion server with a cache for accumulating therein a plurality of pieces of medical image data, the protocol conversion server can store medical image data, once transferred to a terminal, in the cache and can transfer the medical image data to another terminal immediately after receipt of request from the terminal, whereby transfer of medical image data can be executed at a higher efficiency.

Further when the protocol conversion server is arranged to convert the format of the medical image data to a predetermined format, medical image data can be converted to medical image data in a desired format conforming to the terminal, whereby efficiency in diagnosis can be improved.

DESCRIPTION OF THE PREFERRED EMBODIMENTS

Embodiments of the present invention will be described with reference to the drawings, hereinbelow.

Figure 1:
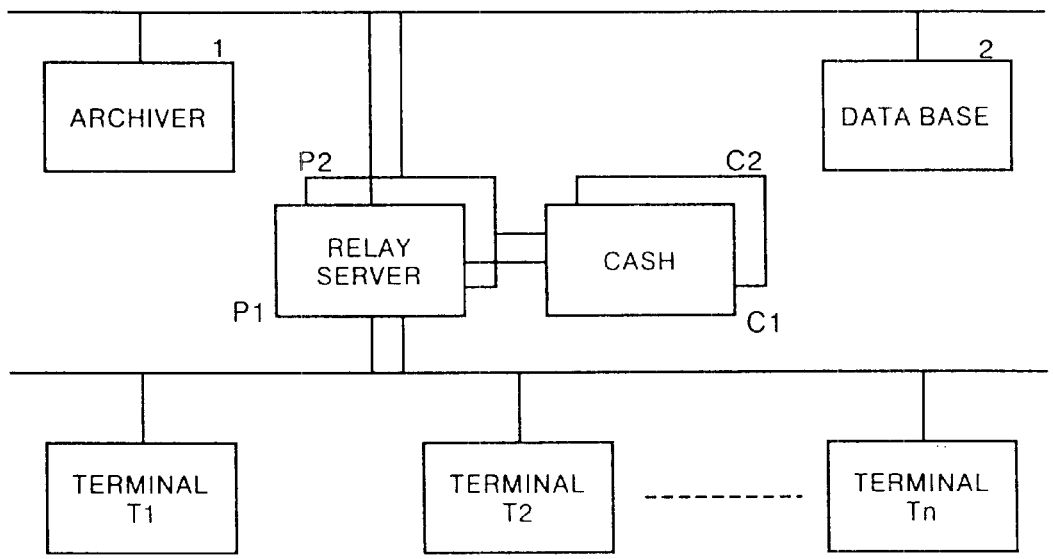
FIG. 1 is a schematic view showing an image transfer system in accordance with a first embodiment of the present invention.

FIG. 1 shows an image transfer system in accordance with a first embodiment of the present invention. In FIG. 1, the image transfer system in accordance with the first embodiment of the present invention comprises an archiver (image server) 1 in which a plurality of pieces medical image data are stored, a data base 2 in which a plurality of pieces medical image data are stored, and a plurality of terminals T1 to Tn (sometimes represented by terminal T1, hereinbelow) which are connected through a network. Further a pair of relay servers P1 and P2 are connected between the terminals T1 to Tn and the archiver 1 and between the terminals T1 to Tn and the data base 2. Medical image data is transferred between the terminals T1 to Tn, the relay servers P1 and P2, the archiver 1 and the data base 2 on the DICOM standard communication system.

The relay servers P1 and P2 send a request for transfer of a desired piece of medical image data to the archiver 1 or the data base 2 on the basis of a request from a terminal and transfers the desired piece of medical image data, transferred to the relay server from the archiver 1 or the data base 2, to the terminal. The relay servers P1 and P2 are provided with caches C1 and C2 and can accumulate pieces of medical image data to be transferred to the terminals T1 to Tn in the chaches C1 and C2.

The operation of the image transfer system of this embodiment will be described, hereinbelow. When a request for a desired piece of medical image data is input into the terminal T1, the request is sent to one of the relay servers P1 and P2. When it is set in advance that the request from the terminals T1 to Tn is to be first sent to the relay server P1, the request is sent to the relay server P1. The relay server P1 then sends a request for transfer of the desired piece of medical image data to the archiver 1. When there is stored the desired piece of medical image data in the archiver 1, the archiver 1 transfers the desired piece of medical image data to the relay server P1. The relay server P1 stores the medical image data in the cache C1 and at the same time transfers the same to the terminal T1. Then the medical image data can be observed by displaying the same on a CRT or the like at the terminal T1.

On the other hand, when there is not stored the desired piece of medical image data in the archiver 1, the archiver 1 sends a message describing the condition to the relay server P1. Upon receipt of the message, the relay server P1 sends a request for transfer of the desired piece of medical image data to the data base 2. When there is stored the desired piece of medical image data in the data base 2, the data base 2 transfers the desired piece of medical image data to the relay server P1. The relay server P1 transfers the medical image data to the terminal T1. When there is not stored the desired piece of medical image data either in the data base 2, the relay server P1 sends a message describing the condition to the terminal T1.

When a request for transfer of the same piece of medical image data is subsequently sent to the relay server P1 from another terminal (e.g., T2), the relay server P1 transfers the medical image data stored in the cache C1 to the terminal T2 without sending the request to the archiver 1 or the data base 2. Accordingly the terminal T2 can obtain the desired medical image data more quickly. Further by once storing a plurality of pieces of medical image data in the caches C1 and C2 before transferring the pieces of medical image data to the archiver 1 or the data base 2 from the terminals T1 to Tn when a request for transfer of medical image data is input to the relay servers P1 and P2 at one time from a plurality of the terminals T1 to Tn, and transferring in sequence the pieces of medical image data to the archiver 1 or the data base 2, data traffic between the relay servers P1 and P2 and the archiver 1 or the data base 2 can be reduced and transfer speed of the medical image data from the terminals T1 to Tn to the archiver 1 or the data base 2 can be apparently increased.

Thus, in the image transfer system of this embodiment, since relay servers P1 and P2 which make access to the archiver 1 or the data base 2 to execute transfer of the medical image data on the basis of instruction from the terminals T1 to Tn are provided between the terminals T1 to Tn and the archiver 1 or the data base 2, the terminals T1 to Tn have only to send the request asking for transfer of a desired piece of medical image data and need not repeatedly send the same request to other image servers even if the desired piece of medical image data is not stored in the first image server.

Further, by providing the image transfer system with a plurality of such relay servers P1 and P2, when a plurality of requests are sent to one of the relay servers from a plurality of terminals T1 to Tn at one time, the relay server can distribute the requests to other relay servers, whereby transfer of medical image data can be executed at a high efficiency. Further even if one of the relay servers P1 and P2 fails, the other relay servers can act for the fault relay server.

Figure 2:
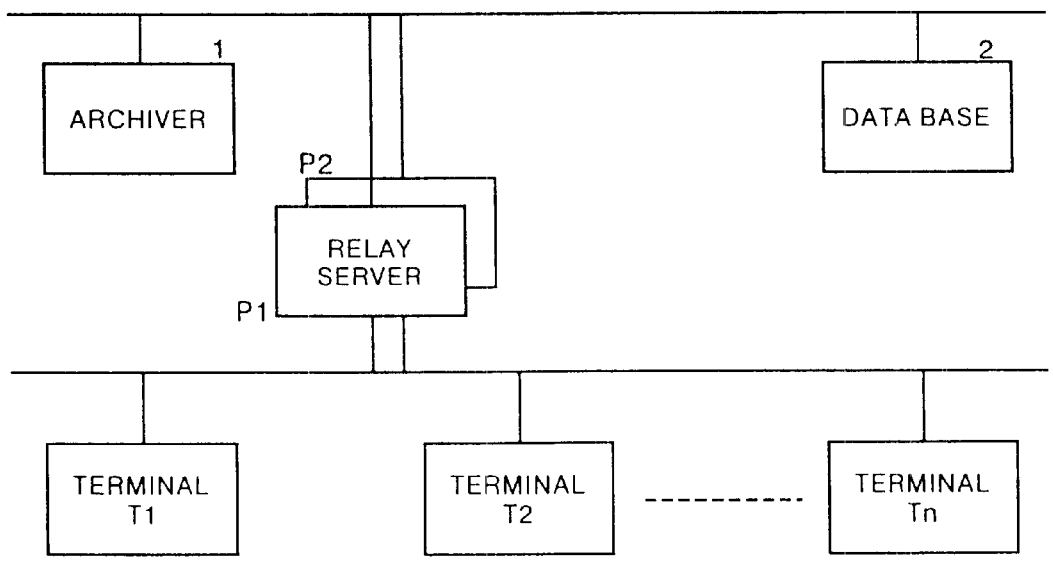
FIG. 2 is a schematic view showing an image transfer system in accordance with a second embodiment of the present invention.

FIG. 2 shows an image transfer system in accordance with a second embodiment of the present invention. The image transfer system of the second embodiment differs from that of the first embodiment only in that the relay servers P1 and P2 are not provided with the caches C1 and C2. In this embodiment, the relay server P1 must send a request for transfer of a desired piece of medical image data to the archiver 1 or the data base 2 each time a request for transfer of the same piece of medical image data is sent to the relay server P1 from the terminals T1 to Tn. However since the image transfer system is provided with a plurality of relay servers P1 and P2, when a plurality of requests are sent to one of the relay servers from a plurality of terminals T1 to Tn at one time, the relay server can distribute the requests to other relay servers, whereby transfer of medical image data can be executed at a high efficiency. Further even if one of the relay servers P1 and P2 fails, the other relay servers can act for the fault relay server.

Though, in the first embodiment described above, the relay servers P1 and P2 do not send a request for transfer of medical image data to the archiver 1 or the data base 2 until a request for transfer of a desired medical image data is input from the terminals T1 to Tn, the relay servers P1 and P2 may send a request for transfer of medical image data to the archiver 1 or the data base 2 prior to receipt of a request for transfer of a desired medical image data from the terminals T1 to Tn. In this case, the pieces of medical image data transferred to the relay servers P1 and P2 from the archiver 1 or the data base 2 are accumulated in the cashes C1 and C2. For example, the relay servers P1 and P2 may periodically send a request for transfer of medical image data to the archiver 1 and the data base 2 and the archiver 1 and the data base 2 may transfer to the relay servers P1 and P2 the pieces of medical image data which are accumulated therein after the preceding request. Then the relay servers P1 and P2 accumulate the pieces of medical image data transferred in the caches C1 and C2. Otherwise, the relay servers P1 and P2 may send a request for transfer of medical image data to the archiver 1 and the data base 2 upon receipt of a message describing that a new piece of medical image data is stored in the archiver 1 or the data base 2 from them.

When the relay servers P1 and P2 are thus arranged to receive transfer of medical image data and accumulate the transferred pieces of medical image data in the caches C1 and C2 prior to a request from the terminals T1 and T2, the relay servers P1 and P2 can transfer a desired piece of medical image data immediately after receipt of the request from the terminal without sending a request for transfer of medical image data to the archiver 1 or the data base 2, whereby the terminals T1 to Tn can obtain the desired piece of medical image data more quickly.

Further, the relay servers P1 and P2 may receive and store in the caches C1 and C2 newly created medical image data when the newly created medical image data is transferred from an image read-out system (not shown) to the archiver 1 or the data base 2 by way of the relay servers P1 and P2.

When medical image data is created on a network in a hospital, a medical system in the hospital transfers order information describing the name of the patient, the part to be radiographed and the like to the department of radiology according to a request of a doctor, and the department of radiology takes a radiograph of the patient according to the order information, generates a piece of medical image data by use of an image read-out system, and stores the medical image data thus generated in the archiver 1 or the data base 2 by way of the network. The medical system may transfer the order information also to the relay servers P1 and P2. Further when the department of radiology generates medical image data, information on the name of the patient, the part to be radiographed and the like is attached to the medical image data. The attached information may be transferred to the relay servers P1 and P2. In such cases, the relay servers P1 and P2, on the basis of the order information or the attached information, send a request for transfer of related medical image data such as past medical image data of the patient and the like to the archiver 1 or the data base 2 prior to recipt of a request from the terminals T1 to Tn. Upon receipt of the request, the archiver 1 or the data base 2 transfer the related medical image data to the relay servers P1 and P2 and the relay servers P1 and P2 stores the related medical image data in the caches C1 and C2. When making diagnosis, a doctor generally requires not only the medical image data which he ordered but also the related medical image data. In this case, since the related medical image data has been stored in the caches C1 and C2, the relay servers P1 and P2 can transfer the related medical image data immediately upon receipt of the request from the terminals T1 to Tn without sending a request for transfer of the related medical image data to the archiver 1 or the data base 2, whereby the related medical image data can be quickly transferred to the terminals T1 to Tn.

Though, in the first and second embodiments described above, a pair of relay servers P1 and P2 are provided, three or more relay servers or only a single relay server may be provided. Further, all the relay servers may be provided with a cache or only a part of the relay servers may be provided with a cache.

In the first and second embodiments, when the line between the terminals T1 to Tn and the relay servers P1 and P2 is thick so that a larger amount of information can be transmitted at one time, line traffic between the terminal and the relay server is reduced and transfer of medical image data can be executed at a higher speed.

A third embodiment of the present invention will be described, hereinbelow.

Figure 3:
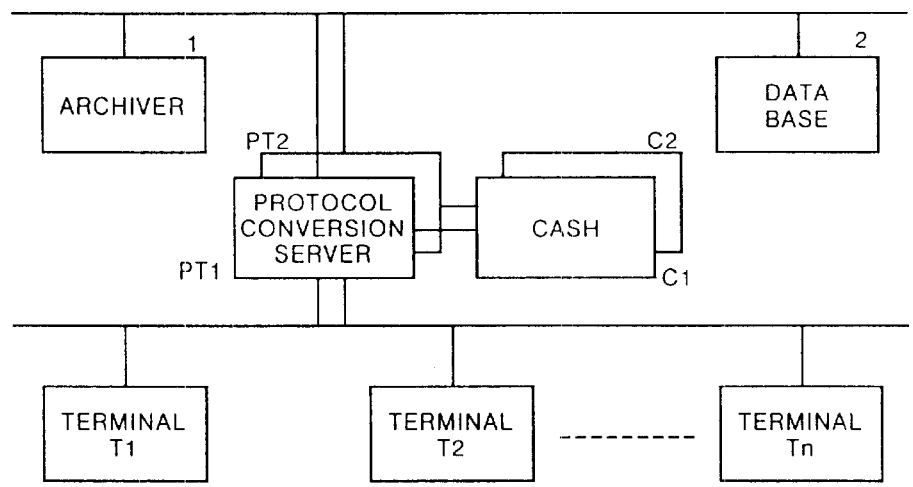
FIG. 3 is a schematic view showing an image transfer system in accordance with a third embodiment of the present invention.

FIG. 3 shows an image transfer system in accordance with a third embodiment of the present invention. In FIG. 3, the image transfer system in accordance with the third embodiment of the present invention comprises an archiver (image server) 1 in which a plurality of pieces medical image data are stored, a data base 2 in which a plurality of pieces medical image data are stored, and a plurality of terminals T1 to Tn (sometimes represented by terminal T1, hereinbelow) which are connected through a network. Further a pair of protocol conversion servers PT1 and PT2 are connected between the terminals T1 to Tn and the archiver 1 and between the terminals T1 to Tn and the data base 2. Medical image data is transferred between the terminals T1 to Tn, the protocol conversion servers PT1 and PT2, the archiver 1 and the data base 2 on the DICOM standard communication system.

The protocol conversion servers PT1 and PT2 send a request for transfer of a desired piece of medical image data to the archiver 1 or the data base 2 on the basis of a request from a terminal and transfers the desired piece of medical image data, transferred to the protocol conversion server from the archiver 1 or the data base 2, to the terminal. At this time, the desired piece of medical image data is transferred from the archiver 1 or the data base 2 to the protocol conversion servers PT1 and PT2 on the DICOM standard protocol, and the protocol conversion servers PT1 and PT2 convert the desired piece of medical image data to medical image data on a generalized protocol (e.g., http) and transfer the converted medical image data to the terminal. Conversely the protocol conversion servers PT1 and PT2 convert medical image data on the generalized protocol transferred to the protocol conversion servers PT1 and PT2 from the terminal to medical image data on the DICOM standard protocol and transfer the converted medical image data to the archiver 1 or the data base 2. Accordingly, medical image data can be observed by the web browser at the terminals T1 to Tn. Further the protocol conversion servers PT1 and PT2 are provided with chaches C1 and C2 and can accumulate pieces of medical image data to be transferred to the terminals T1 to Tn in the chaches C1 and C2.

The operation of the image transfer system of this embodiment will be described, hereinbelow. When a request for a desired piece of medical image data is input into the terminal T1, the request is sent to one of the protocol conversion servers PT1 and PT2. When it is set in advance that the request from the terminals T1 to Tn is to be first sent to the protocol conversion server PT1, the request is sent to the protocol conversion server PT1. The protocol conversion server PT1 then sends a request for transfer of the desired piece of medical image data to the archiver 1. When there is stored the desired piece of medical image data in the archiver 1, the archiver 1 transfers the desired piece of medical image data to the protocol conversion server PT1. The protocol conversion server PT1 stores the medical image data in the cache C1 and at the same time transfers the same to the terminal T1 after converting the medical image data to medical image data on a generalized protocol conforming to the web browser. Then the medical image data can be observed by displaying the same on a CRT or the like at the terminal T1 by use of the web browser. The cache C1 may store the medical image data on the DICOM as it is or may store the same in the converted state.

On the other hand, when there is not stored the desired piece of medical image data in the archiver 1, the archiver 1 sends a message describing the condition to the protocol conversion server PT1. Upon receipt of the message, the protocol conversion server PT1 sends a request for transfer of the desired piece of medical image data to the data base 2. When there is stored the desired piece of medical image data in the data base 2, the data base 2 transfers the desired piece of medical image data to the protocol conversion server PT1. The protocol conversion server PT1 transfers the medical image data to the terminal T1 after converting the medical image data to medical image data on a generalized protocol. When there is not stored the desired piece of medical image data either in the data base 2, the protocol conversion server PT1 sends a message describing the condition to the terminal T1.

When a request for transfer of the same piece of medical image data is subsequently sent to the protocol conversion server PT1 from another terminal (e.g., T2), the protocol conversion server PT1 transfers the medical image data stored in the cache C1 to the terminal T2 without sending the request to the archiver 1 or the data base 2. Accordingly the terminal T2 can obtain the desired medical image data more quickly. Further by once storing a plurality of pieces of medical image data in the caches C1 and C2 before transferring the pieces of medical image data to the archiver 1 or the data base 2 from the terminals T1 to Tn, transfer speed of the medical image data from the terminals T1 to Tn to the archiver 1 or the data base 2 can be apparently increased.

Thus, in the image transfer system of this embodiment, since the image transfer system is provided between the terminals T1 to Tn and the archiver 1 or the data base 2 with the protocol conversion servers which convert the DICOM standard protocol to a generalized protocol such as http, ftp and the like, the medical image data transferred on the DICOM standard protocol can be displayed at the terminals T1 to Tn by inexpensive web browser. On the other hand, the medical image data on the generalized protocol transferred to the protocol conversion servers PT1 and PT2 from the terminal is converted to medical image data on the DICOM standard protocol by the protocol conversion servers PT1 and PT2 and is transferred to the archiver 1 or the data base 2. Accordingly, medical image data can be observed through an inexpensive system such as a general-purpose personal computer at the terminals T1 to Tn and medical image data can be transferred through Internet, whereby an exclusive network is unnecessary and the system can be formed at low cost.

Further, by providing the image transfer system with a plurality of such protocol conversion servers PT1 and PT2, when a plurality of requests are sent to one of the protocol conversion servers PT1 and PT2 from a plurality of terminals T1 to Tn at one time, the protocol conversion server can distribute the requests to other protocol conversion server, whereby transfer of medical image data can be executed at a high efficiency. Further even if one of the protocol conversion servers PT1 and PT2 fails, the other protocol conversion server can act for the fault protocol conversion server.

A fourth embodiment of the present invention will be described, hereinbelow.

Figure 4:
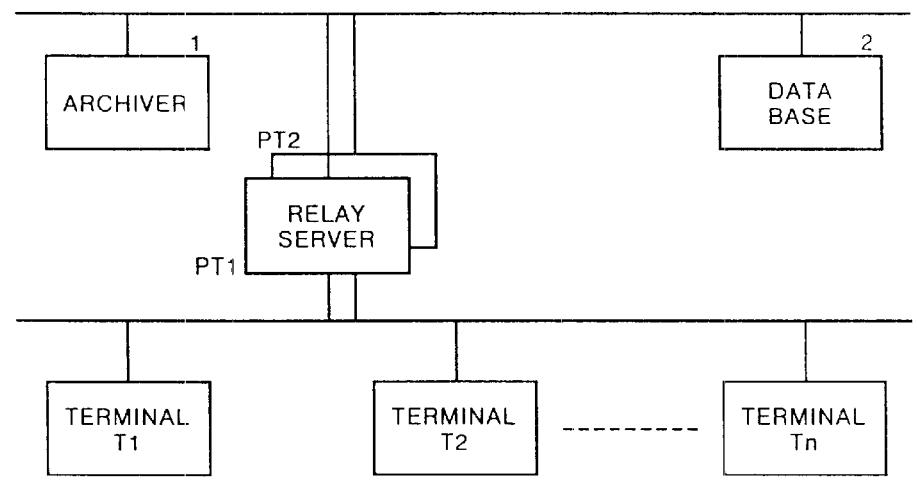
FIG. 4 is a schematic view showing an image transfer system in accordance with a fourth embodiment of the present invention.
Figure 5:
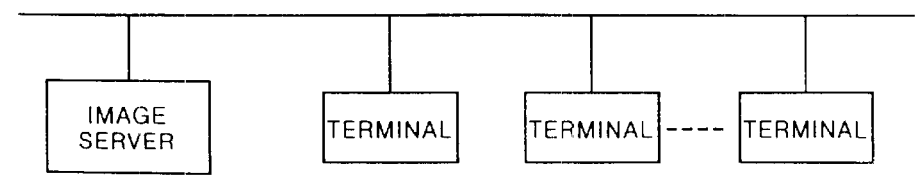
FIG. 5 is a schematic view showing a conventional image transfer system.

FIG. 4 shows an image transfer system in accordance with a fourth embodiment of the present invention. The image transfer system of the fourth embodiment differs from that of the third embodiment only in that the protocol conversion servers PT1 and PT2 are not provided with the caches C1 and C2. In this embodiment, the protocol conversion servers PT1 and PT2 must send a request for transfer of a desired piece of medical image data to the archiver 1 or the data base 2 each time a request for transfer of the same piece of medical image data is sent to the protocol conversion servers PT1 and PT2 from the terminals T1 to Tn. However since the image transfer system is provided with a plurality of protocol conversion servers PT1 and PT2, when a plurality of requests are sent to one of the protocol conversion servers PT1 and PT2 from a plurality of terminals T1 to Tn at one time, the protocol conversion server can distribute the requests to other protocol conversion server, whereby transfer of medical image data can be executed at a high efficiency. Further even if one of the protocol conversion servers PT1 and PT2 fails, the other protocol conversion server can act for the fault relay server.

Though, in the third and fourth embodiments described above, a pair of protocol conversion servers PT1 and PT2 are provided, three or more protocol conversion servers or only a single protocol conversion server may be provided. Further, all the protocol conversion servers may be provided with a cache or only a part of the protocol conversion servers may be provided with a cache.

In the third and fourth embodiments, when the line between the terminals T1 to Tn and the protocol conversion servers PT1 and PT2 is thick so that a larger amount of information can be transmitted at one time, line traffic between the terminal and the protocol conversion server is reduced and transfer of medical image data can be executed at a higher speed.

Further though, in third and fourth embodiments, the protocol conversion servers PT1 and PT2 convert only the protocol of the medical image data, the protocol conversion servers PT1 and PT2 may, when the medical image data is in a format which cannot be displayed by the web browser, convert the format of the medical image data to a format which can be displayed by the web browser, e.g., JPEG, before transferring the medical image data to the terminals T1 to Tn. Further it is possible to arrange the protocol conversion servers PT1 and PT2 to, when the medical image data is too large in data size, compress the data size of the medical image data before transferring the medical image data to the terminals T1 to Tn. Further, when medical image data and diagnostic report or the like are to be displayed in one frame, it is possible to arrange the protocol conversion servers PT1 and PT2 so that they receive the diagnostic report from the data base 2, combines the diagnostic report with the medical image data to form a HTML document and transfers the HTML document to the terminals T1 to Tn.

What is claimed is:

1. An image transfer system comprising:
   one or more image servers which store medical image data,
   at least one terminal for instructing transfer of the medical image data from the image server to the terminal and transfer of the medical image data from the terminal to the image server on a DICOM type communication system, and
   a relay server intervening between the terminal and the image servers, and accessing one of the image servers on the basis of an instruction from the terminal to execute a transfer of the medical image data.

2. An image transfer system as defined in claim 1, further comprising a plurality of said relay servers.

3. An image transfer system as defined in claim 1, wherein the relay server comprises a cache for accumulating a plurality of pieces of medical image data.

4. An image transfer system as defined in claim 2, wherein the relay servers comprise a cache for accumulating a plurality of pieces of medical image data.

5. An image transfer system comprising:
   one or more image servers storing medical image data,
   at least one terminal for instructing transfer of the medical image data from the image server to the terminal and transfer of the medical image data from the terminal to the image server on a DICOM type communication system, and
   a relay server intervening between the terminal and the image servers, receiving the transfer of medical image data prior to instruction from the terminal, and comprising a cache for accumulating a plurality of pieces of medical image data.

6. An image transfer system as defined in claim 5, further comprising a plurality of said relay servers.

7. An image transfer system comprising:
   one or more image servers storing medical image data,
   at least one terminal for instructing transfer of the medical image data from the image server to the terminal and transfer of the medical image data from the terminal to the image server on a DICOM standard communication system,
   a protocol conversion server intervening between the terminal and the image servers, transferring medical image data, transferred from the image servers, to the terminal after converting the DICOM standard protocol of the medical image data to a generalized protocol, and transferring the medical image data, transferred from the terminal, to the image servers after converting the generalized protocol of the medical image data to the DICOM standard protocol.

8. An image transfer system as defined in claim 7, further comprising a plurality of said protocol conversion servers.

9. An image transfer system as defined in claim 7, wherein the protocol conversion server comprises a cache for accumulating a plurality of pieces of medical image data.

10. An image transfer system as defined in claim 8, wherein the protocol conversion servers each comprise a cache for accumulating a plurality of pieces of medical image data.

11. An image transfer system as defined in claim 7, wherein the protocol conversion server converts the format of the medical image data to a predetermined format and then transfers the converted medical image data to the terminal.

12. An image transfer system as defined in claim 8, wherein the protocol conversion servers convert the format of the medical image data to a predetermined format and then transfers the converted medical image data to the terminal.

13. An image transfer system as defined in claim 9, wherein the protocol conversion server converts the format of the medical image data to a predetermined format and then transfers the converted medical image data to the terminal.

14. An image transfer system as defined in claim 10, wherein the protocol conversion servers convert the format of the medical image data to a predetermined format and then transfer the converted medical image data to the terminal.

* * * * *